US008680060B2

(12) United States Patent
Awada et al.

(10) Patent No.: US 8,680,060 B2
(45) Date of Patent: Mar. 25, 2014

(54) COMPOSITIONS AND METHODS FOR CONTROLLING PESTS WITH GLYCOLIPIDS (75) Inventors: Salam M. Awada, Logan, UT (US); Mohamed M. Awada, Logan, UT (US); Rex S. Spendlove, Millville, UT (US)

(73) Assignee: Agscitech Inc., Logan, UT (US)

( * ) Notice: Subject to any disclaimer, the term of this patent is extended or adjusted under 35 U.S.C. 154(b) by 3 days.

(21) Appl. No.: 13/171,960

(22) Filed: Jun. 29, 2011

(65) Prior Publication Data
US 2012/0058895 A1 Mar. 8, 2012

Related U.S. Application Data (63) Continuation of application No. 11/141,669, filed on May 31, 2005, now Pat. No. 7,994,138.

(60) Provisional application No. 60/575,913, filed on Jun. 1, 2004, provisional application No. 60/604,139, filed on Aug. 23, 2004.

(51) Int. Cl.
A01N 43/16 (2006.01)

(52) U.S. Cl.
USPC ............................. 514/23; 424/93; 424/93.41

(58) Field of Classification Search
USPC .................................... 424/93, 93.41; 514/23
See application file for complete search history.

(56) References Cited

U.S. PATENT DOCUMENTS

| 3,450,818 | A | * | 6/1969 | Edwards et al. | 514/469 |
|---|---|---|---|---|---|
| 4,084,951 | A | * | 4/1978 | Gregory | 504/193 |
| 4,559,074 | A | * | 12/1985 | Clarke | 71/24 |
| 4,628,030 | A | * | 12/1986 | Kaeppeli et al. | 435/101 |
| 5,455,232 | A | | 10/1995 | Piljac et al. | |
| 5,747,416 | A | | 5/1998 | McArdle | |
| 5,767,090 | A | | 6/1998 | Stanghellini et al. | |
| 6,015,553 | A | | 1/2000 | Germida et al. | |
| 6,063,406 | A | | 5/2000 | Hornack | |
| 6,291,156 | B1 | | 9/2001 | Estruch et al. | |
| 6,417,163 | B1 | | 7/2002 | Heins et al. | |
| 2002/0010157 | A1 | * | 1/2002 | Duan et al. | 514/78 |
| 2003/0022242 | A1 | | 1/2003 | Anderson | |
| 2004/0234657 | A1 | | 11/2004 | Rowley et al. | |

FOREIGN PATENT DOCUMENTS

| CN | 1434002 A | * | 8/2003 |
|---|---|---|---|
| JP | 10-75796 A | | 3/1998 |
| WO | 97/25866 A | | 7/1997 |
| WO | 98/50422 A | | 11/1998 |
| WO | 00/29426 A | | 5/2000 |

OTHER PUBLICATIONS

Kim et al., In vivo control and in vitro antifungal acitivuty of rhamnolipid B, a glycolipid antibiotic, against *Phytophthora capsici* and *Collectotrichum orbiculare*, 2002, Pest Management Science, vol. 56, pp. 1029-1035.*
Cosson, et al., *Pseudomonas aeruginosa* Virulence Analyzed in a *Dictyostelium discoideum* Host System, Jun. 2002, Journal of Bacteriology, vol. 184 iss. 11, pp. 3027-3033.*
Sun et al., A perliminary study on the mechanism of harmful algal bloom mitigation by use of sophorolipid treatment, Jun. 16, 2004, Journal of Experimental Marine Biology and Ecology, vol. 304, pp. 35-49.*
AU 2005-249537 Office Action Mailed Aug. 15, 2007.
AU 2005-249537 Office Action Mailed Sep. 19, 2008.
CA 25666864 Office Action Mailed Nov. 3, 2009.
KR 10038285 Publication May 15, 2001.
U.S. Appl. No. 11/209,132 Office Action Mailed Jan. 28, 2008.
U.S. Appl. No. 11/209,132 Final Office Action Mailed May 14, 2009.
U.S. Appl. No. 11/209,132 Office Action Mailed Oct. 6, 2009.
U.S. Appl. No. 11/209,132 Final Office Action Mailed Apr. 13, 2011.
Stanghellini M E et al., "Their Identity and potential Efficacy in the Biological Control of Zoosporic Plant Pathogens", Plant Disease, American Phytopathological Society, St. Paul, MN,US, vol. 81, No. 1, pp. 4-12 Jan. 1, 1997.
Cosson Pierre et al., "*Pseudomonas aeruginosa* Virulence Analyzed in a *Dictyostelium discoideum* Host System", Journal of Bacteriology, vol. 184, No. 11, pp. 3027-3033, Jun. 2002.
European Supplementary Search report dated Nov. 6, 2009, as issued in application No. 05758145.6(1 750 738).
U.S. Appl. No. 11/141,669 Office Action Mailed Sep. 17, 2007.
U.S. Appl. No. 11/141,669 Final Office Action Mailed Apr. 1, 2008.
U.S. Appl. No. 11/141,669 Office Action Mailed Dec. 9, 2008.
U.S. Appl. No. 11/141,669 Notice of Allowance Mailed Mar. 31, 2011.
U.S. Appl. No. 11/141,669 Notice of Allowance Mailed Mar. 5, 2010.
Bodour et al, Structure and Characterization of Flavolipids, a Novel Class of Biosurfactants Produced by *Flavobacterium* sp. Strain MTN11 Jan. 2004, Applied and Environmental Microbiology, vol. 70 No. 1, pp. 114-120.

* cited by examiner

*Primary Examiner* — Ali Soroush
(74) *Attorney, Agent, or Firm* — Maschoff Brennan (57) ABSTRACT

Biosurfactants produced by microbes are used to control pests. The biosurfactants can be produced by cultivating a biosurfactant-producing microbe, producing a fermentation broth, and obtaining the biosurfactant from the fermentation broth. Alternately, the biosurfactants can be produced in situ in the environment of the pests by applying a carbon substrate to the pests' environment, which permits naturally-occurring biosurfactant-producing microbes to grow and to generate the biosurfactants. The biosurfactants have pesticidal qualities, and can be used to control a variety of pests, while being biodegradable and otherwise avoiding adverse environmental effects that have often been associated with conventional synthetic pesticides.

18 Claims, 2 Drawing Sheets

COMPOSITIONS AND METHODS FOR CONTROLLING PESTS WITH GLYCOLIPIDS

CROSS-REFERENCE

This application is a continuation of U.S. patent application Ser. No. 11/141,669, filed May 31, 2005, which claims benefit of U.S. Provisional Patent Application Ser. No. 60/575,913, filed Jun. 1, 2004, and of U.S. Provisional Patent Application Ser. No. 60/604,139, filed Aug. 23, 2004, which applications are incorporated herein by specific reference in their entirety.

BACKGROUND

Although chemical pesticides are valuable in the control of pests, their use poses many problems. They tend to harm non-target organisms such as humans, domestic animals, beneficial insects, and wildlife. In addition, their residues tend to remain on the crop and may accumulate in the soil, water, or air. Another concern is the development of resistance to pesticides by the targeted organisms. Due to the serious environmental problems associated with chemical pesticides, the demand for safer pesticides and alternate pest control strategies is increasing.

It has become widely known in the art that certain live biological control agents (bacteria, phage, bacteriophages) have some use in pest control. The success of these biological control agents depends on understanding the biology of these agents and of the target pest. Several limitations are associated with the use of these biological agents according to conventional techniques. One of the limitations is that some of the biologic control agents are opportunistic pathogens against humans or animals. Another constraint is the competition between the native organisms (beneficial or pathogens) in the ecosystem and the control agents. In many cases, the control agent is not able to compete in the environment and the efficacy of the treatment is questionable.

U.S. Pat. No. 5,767,090 describes the use of rhamnolipids against the transitional zoosporic stage of zoosporic fungi. Although rhamnolipids are very effective against this motile stage of the pathogenic fungi, successful treatment in commercial crops production depends greatly on application time and repetitive applications are sometimes necessary to achieve the desired control. During wet conditions foliar application may be impractical and repetitive applications significantly increases production cost.

SUMMARY

The present invention relates to methods and compositions, based upon natural microbial biosurfactants, for controlling pests. Examples of the pests treated with the biocontrol agents include insects such as ants, aphids, thrips, whiteflies, scales, lice, cockroaches, termites, houseflies, mosquitoes, etc; arachnids such as mites, spiders, ticks; nematodes; mollusks; amoeba; parasites; and algae. The agents for controlling pests according to the invention include natural pesticides (biopesticides) derived of microbial origin. Biopesticides are inherently less harmful than conventional pesticides. They often biodegrade quickly, therefore resulting in low exposures and largely avoiding the pollution problems caused by conventional pesticides.

Embodiments of the invention extend to the use of naturally occurring microbial biosurfactant compounds to control pests. The invention also extends to methods of controlling pests using biosurfactant-producing microorganisms. The invention further encompasses the compositions themselves, as well as the methods for manufacturing or producing the compositions and their application to pest control as disclosed herein. Other objects of the invention may be apparent to one of skill in the art upon learning of the invention described herein.

In another embodiment of the invention, formulations and treatments to control pests are achieved by the addition of carbon, or organic, substrates, such as oil or fatty acids, to target areas (before or during infestation) to support the growth of biosurfactant-producing organisms as well as to produce the desired biosurfactants on site to achieve the objective of the invention. Natural biosurfactant-producing organisms at the site of application (soil, aquatic system, plant parts, etc) will produce biosurfactants while utilizing the carbon substrate. During this process, the biosurfactant produced will destroy or paralyze pests in the targeted area. According to the invention, it is not necessary to pre-inoculate the targeted site or the carbon substrate mixture with biosurfactant-producing organisms.

Microbial biosurfactants are compounds produced by variety of microorganisms such as bacteria, fungi, and yeasts. Biosurfactants form an important class of secondary metabolites that occur in many microorganisms such as *Pseudomonas* species (*P. aeruginosa, P. putida, P. florescens, P. fragi, P. syringae*); *Flavobacterium* spp.; *Bacillus* spp. (*B. subtilis, B. pumillus, B. cereus, B. licheniformis*); *Candida* species (*C. albicans, C. rugosa, C. tropicalis, C. lipolytica, C. torulopsis*); *Rhodococcus* sp.; *Arthrobacter* spp.; *campylobacter* spp.; *cornybacterium* spp. and so on.

Biosurfactants are biodegradable and can be easily and cheaply produced using selected organisms on renewable substrates. Most biosurfactant-producing organisms produce biosurfactants in response to the presence of hydrocarbon source (e.g. oils, sugar, glycerol, etc) in the growing media. Other media components can also affect biosurfactant production significantly. For example, the production of rhamnolipids by the bacteria *Pseudomonas aeruginosa* can be increased if nitrate is used as a source of nitrogen rather than ammonium. Also the concentration of iron, magnesium, sodium, and potassium; the carbon:phosphorus ratio, and agitation greatly affect rhamnolipid production.

Biosurfactants include low-molecular-weight glycolipids (GLs), lipopeptides (LPs), flavolipids (FLs), phospholipids, and high-molecular-weight polymers such as lipoproteins, lipopolysaccharide-protein complexes, and polysaccharide-protein-fatty acid complexes. Biosurfactants have a great deal of structural diversity. The common lipophilic moiety of a biosurfactant molecule is the hydrocarbon chain of a fatty acid, whereas the hydrophilic part is formed by ester or alcohol groups of neutral lipids, by the carboxylate group of fatty acids or amino acids (or peptides), organic acid in the case of flavolipids, or, in the case of glycolipids, by the carbohydrate.

According to the embodiments of the invention, these compounds may also be synthesized by standard organic synthesis methods.

In one embodiment, a single biosurfactant or a mixture of different biosurfactants may be used in a formulation to perform the functions and achieve the results disclosed herein.

Co-pending U.S. Provisional Patent Application Ser. No. 60/604,139, filed Aug. 23, 2004, is incorporated herein by reference and describes biosurfactants (e.g. GLs, FLs, and LPs etc) having a powerful penetrating capabilities. It has been discovered that an important characteristic of these biosurfactants or biopesticides is that they are able to penetrate tissues or cells. This is a very important factor that influences effectiveness of pesticides. In general, the effectiveness of pesticides can be significantly enhanced if they are able to readily spread on the treated surface and to penetrate into the pest (e.g., into the insects' cuticle). According to embodiments of this invention, the biopesticide is able to penetrate through pests' tissues sufficiently and to be effective in lesser amounts without the use of adjuvants. It has been found that at concentrations above the critical micelle concentration, the biosurfactant are able to penetrate more effectively into treated objects.

In this invention, we have unexpectedly discovered that some natural and non-toxic biosurfactants such as rhamnolipids have unique mode of action against some pests and parasites and this broad-spectrum activity differs from conventional pesticides mode of action.

The development of the natural biopesticides of the invention, which can be produced in high amounts using selected microorganisms for pest control, represents a significant advancement in the art. As noted above, pests can be controlled using either the biosurfactant-producing organisms as a biocontrol agent or by the biosurfactants themselves. In addition, pests control can be achieved by the use of specific substrates to support the growth of biosurfactant-producing organisms as well as to produce biosurfactants pesticidal agents. Thus, according to the invention, the microbial biosurfactants' glycolipids, such as rhamnolipids, sophorlipids, trehalose lipids; flavolipids; lipopeptides; etc., as pesticidal agents have the potential to reduce the need for and use of synthetic pesticides.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

The foregoing and following information as well as other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

arranged in accordance with at least one of the embodiments described herein, and which arrangement may be modified in accordance with the disclosure provided herein by one of ordinary skill in the art.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The present invention is directed to compositions and methods for controlling pests, and, more particularly, to pesticides derived from natural substances, such as microbial or fermentation metabolites. According to embodiments of the invention, the produced fermentation broth containing the microbial biosurfactant may be used without extraction or purification. If desired, extraction and purification of the biosurfactants can be easily achieved using standard extraction methods or techniques described in the literature.

In one aspect of the invention, fermentation broth or the purified biosurfactants, e.g., GLs, FLs, LPs, etc., may be used to protect crop plants, homes, structures, soils, aquatic systems, ponds, fish aquariums, humans, or animals by controlling harmful pests. As used herein, the term "control" used in reference to the activity produced by the biosurfactants or biosurfactant-producing organisms extends to the act of killing, disabling or immobilizing pests or otherwise rendering the pests substantially incapable of causing harm.

In another aspect of the invention, biosurfactant-producing organisms, e.g., *Pseudomonas* spp. may be added to the soil, plants' growing medium, plants, aquatic medium, or any area to be treated. The organisms can grow onsite and produce the biosurfactants to control the pests targeted as described in this invention. The cultures may be mixed with growth enhancement substances to aid in their growth and the production of the microbial biosurfactants. Substances such as oil, glycerol, sugar, or other nutrients may also be used.

In another embodiment of the invention, carbon substrate to support the growth of biosurfactant producing organisms is added to the pest infested areas, soil, plants' growing medium, plant parts, aquatic medium, or any area to be treated. Biosurfactant producing organisms can grow on the substrate to produce biosurfactant in place and control the targeted pests as described in this invention. It is not necessary to add biosurfactant-producing organisms to the substrate. Natural biosurfactant producing organisms found at the site of application will be able to grow and produce the biosurfactant. Examples of carbon substrates that can be added to the targeted areas include, but not limited to, organic carbon sources such as natural or synthetic oil including used frying oil; fat; lipid; wax (natural or paraffin); fatty acids such as lauric; myristic, etc; fatty acid alcohol such as lauryl alcohol; amphiphilic esters of fatty acids with glycerol such as glyceryl monolaurate; glycol esters of fatty acid such as polyethylene monostearate; fatty acid amines such as lauryl amine; fatty acid amides; hexanes; glycerol; glucose; etc. It is preferable to use water insoluble carbon substrate to encourage excessive production of the biosurfactants. In addition to the carbon substrate, nutrients such as vitamins, inorganic minerals may also be added to the substrate to encourage biosurfactant-producing organisms growth. Although it is not necessary, it is preferable to spike or amend the carbon substrate with a sufficient amount of specific biosurfactant to initiate the emulsification process and to inhibit or reduce the growth of other competing organisms for the biosurfactant-producing organism and to control pests. An illustrative but not restrictive example would be the addition of 60-100 mg/l rhamnolipid biosurfactant in the final diluted oil substrate mixture. The diluted mixture is applied to the area to be treated. This method aids in growth establishment of *Pseudomonas aeruginosa* or florescens (rhamnolipid producing organisms) population and reduces the chance of growth of its competing or disease causing organisms, the *Phytophthora, nematodes, Bacillus* sp. If it is desired to produce *Syringotoxin lipopeptide* biosurfactants, a small amount of syringotoxins (less than few mg/l) is added to the oil-glycerol substrate. *Syringotoxin* will eliminate many competing organisms and maintain *Pseudomonas syringae* growth while producing the lipopeptide toxins. *Pseudomonas syringae* and *Bacillus subtilis* for instance produce series of lipopeptides biosurfactants referred to as porens. These lipopeptide porens include pseudomycin, syringomycin, tabtoxin, phaseolotoxin, and surfactin. Some lipopeptides are capable of creating holes in cell membranes, cells, and tissues. Due to their powerful activity on cells and tissues, these biosurfactants are very useful in controlling algae, nematodes, insects and other pests. Pseudomycin can be applied as a pre-plant treatment for nematode or insects larvae control in crop production. If it is desired to encourage the growth of *Bacillus subtilis*, a small amount of surfactin biosurfactant is added to the carbon substrate medium to aid in establishment of subtilis population and the production of more surfactin on-site.

The use of carbon substrates to produce biosurfactants at the targeted sites especially in the presence of minute amount of biosurfactant as a biocontrol starting point, greatly enhances the efficacy of the treatment, broadens the biocontrol spectrum against many pathogens, and reduces the frequency and cost of application of the biosurfactant. As it will be described in the examples section, this is very essential for soil treatment applications.

Synthetic surfactants such as alkyl betaines e.g. Lauryl betaine, alkyl sulfates as lauryl sulfate or its salt, alkyl ammonium bromide derivatives, alkyl phenol ethoxylates, alkyl ethylene (or polyethylene) ethoxylates may be used to lower the surface tension and facilitate the utilization of the carbon substrate by the natural biosurfactant-producing organisms but it is preferable to use natural biosurfactants that are able to inhibit the growth of competing organisms and enhance the growth of the specific biosurfactant producing organisms as described in the invention.

Derivatives of these microbial biopesticides or compounds with similar structures or characteristics and able to control pests as also disclosed herein and are encompassed by embodiments of the invention.

It has been observed that some of the mentioned synthetic surfactants above may have inhibitory effects against some pathogens and may also be used as active agents to control pests such as insects, algae, parasitic amoeba, nematodes, weeds or other pests as described in this invention. They may also be used in conjunction with the natural biosurfactants.

According to this invention, biosurfactants (e.g. GLs, FLs, and LPs etc) have a powerful biopesticidal activity against many pests and diseases affecting plants and these biosurfactants also have similar biopesticide activity against pests and diseases affecting humans and animals. Pests controlled include insects, their larvae and eggs; mites; algae (seaweeds, pond algae, and the microscopic algae such as blue-green algae); microbial pests (nematodes, bacteria, fungi, parasites, amoeba, protozoa, viruses, etc); mollusks; worms; and plant weeds. In addition, these biosurfactants may be used to treat human diseases such as ova-parasites and cysts, hair dandruff, etc. In addition, rhamnolipid biosurfactant is an effective spennicide at a concentration of 250 ppm. Examples of animal diseases include, but not limited to, dog's heart worm; fish parasites and microbial infections such as whirling disease caused by the amoeba *Myxobolus*, fish fungal disease (water mold) or green algae; fish protozoa disease such as *Chilodonella*; fish parasites as gill and skin flukes. Also cattle hoof diseases can also be controlled as described in this invention. Animals are treated by dipping or bathing in a biosurfactant solution alone or in the presence of other compounds such as copper or zinc.

The natural biosurfactants' active components may be used according to the invention either alone or combined with other acceptable active or inactive (inert) components that may be used as adjuvants or may have pesticidal activity. It is preferable to use adjuvants or pesticidal components of natural source to complement the natural aspects of the biosurfactants. These components can be either an oil component such as cinnamon oil, clove oil, cottonseed oil, garlic oil, or rosemary oil; another natural surfactant such as *Yucca* or *Quillaja saponins*; or the component may be an aldehyde such as cinnamic aldehyde. Other oils that may be used as a pesticidal component or adjuvants include: almond oil, camphor oil, castor oil, cedar oil, citronella oil, citrus oil, coconut oil, corn oil, eucalyptus oil, fish oil, geranium oil, lecithin, lemon grass oil, linseed oil, mineral oil, mint or peppermint oil, olive oil, pine oil, rapeseed oil, safflower oil, sage oils, sesame seed oil, sweet orange oil, thyme oil, vegetable oil, and wintergreen oil. Other suitable additives, which may be contained in the formulations according to the invention, are all substances, which are customarily used for such preparations. Example of such additives include adjuvants, surfactants, emulsifying agents, plant nutrients, fillers, plasticizers, lubricants, glidants, colorants, pigments, bittering agents, buffering agents, solubility controlling agents, pH adjusting agents, preservatives, stabilizers and ultra-violet light resistant agents. Stiffening or hardening agents may also be incorporated to strengthen the formulations and make them strong enough to resist pressure or force in certain applications such as soil, root flare or tree injection tablets.

Examples of buffering agents include organic and amino acids or their salts. Suitable buffers include citrate, gluconate, tartarate, malate, acetate, lactate, oxalate, aspartate, malonate, glucoheptonate, pyruvate, galactarate, glucarate, tartronate, glutamate, glycine, lysine, glutamine, methionine, cysteine, arginine and a mixture thereof. Phosphoric and phosphorous acids or their salts may also be used. Synthetic buffers are suitable to be used but it is preferable to use natural buffers such as organic and amino acids or their salts listed above.

Examples of solubility control agents or excipients may be used in the formulations to control the release of the active substances may include wax, chitin, chitosan, C12-C20 fatty acids such as myristic acid, stearic acid, palmitic acid; C12-C20 alcohols such as lauryl alcohol, cetyl alcohol, myristyl alcohol, and stearyl alcohol; amphiphilic esters of fatty acids with glycerol, especially monoesters C12-C20 fatty acids such as glyceryl monolaurate, glyceryl monopalmitate; glycol esters of fatty acids such as polyethylene monostearate or polypropylenemonopalmitate glycols; C12-C20 amines such as lauryl amine, myristyl amine, stearyl amine, and amides C12-C20 fatty acids.

Examples of pH adjusting agents include Potassium hydroxide, ammonium hydroxide, Potassium carbonate or bicarbonate, hydrochloric acid, nitric acid, sulfuric acid or a mixture.

Additional components such as an aqueous preparation of a salt as polyprotic acid such as sodium bicarbonate or carbonate, sodium sulfate, sodium phosphate, sodium biphosphate, can be included in the formulation.

According to embodiments of this invention, the microbial biopesticides can be produced and formulated in a variety of ways, including liquid, solids, granular, dust, or slow release products by means that will be understood by those of skill in the art upon learning of the invention disclosed herein.

They may be applied by spraying, pouring, dipping, in the form of concentrated or diluted liquids, solutions, suspensions, powders, and the like, containing such concentrations of the active agent as is most suited for a particular purpose at hand. They may be applied as is or reconstituted prior to use. For example, they may be applied by direct injection into trees or root flares.

Solid formulations of the invention may have different forms and shapes such as cylinders, rods, blocks, capsules, tablets, pills, pellets, strips, spikes, etc. Solid formulations may also be milled, granulated or powdered. The granulated or powdered material may be pressed into tablets or used to fill pre-manufactured gelatin capsules or shells. Semi solid formulations can be prepared in paste, wax, gel, or cream preparations.

For human or animal applications, the formulations may be prepared in liquid, paste, ointment, suppository, capsule or tablet forms and used in a way similar to drugs used in the medicinal drugs industry. The formulations can be encapsulated using components known in the pharmaceutical industry. Encapsulation protects the components from undesirable reactions and helps the ingredients resist adverse conditions in the environment or the treated object or body e.g. stomach.

The compositions according to the invention can be applied to the plants, pests, or soil using various methods of application. Each method of application may be preferred under certain circumstances.

The compositions according to the invention may be used to introduce the active compounds into the soil. These preparations could be incorporated into the soil in the vicinity of the roots of the plants. This could be in the form of liquid, bait, powder, dusting, or granules, or they are inserted in the soil as tablets, spikes, rods, or other shaped moldings.

The compositions according to the invention can be used for treating individual trees or plants. For example, the formulations can be molded in different shapes or forms (solid, paste or gel, or liquid) and introduced into the vascular tissue of the plants. Moldings forms can be as tablets, capsules, plugs, rods, spikes, films, strips, nails, or plates. The shaped moldings can be introduced into pre-drilled holes into the plants or root flares, or they can be pushed or punched into the cambium layer.

Another method of application of the invention is the use of dispensing devices such as syringes, pumps or caulk guns, paste-tubes or plunger tubes for delivering semi-solid formulations (paste, gel, cream) into drilled holes in tree trunks or root flares.

The compositions of the invention can be applied in the form of paste, gel, coatings, strips, or plasters onto the surface of the plant. In one method, a plaster or strip may have the semi-solid formulation, e.g., insecticide placed on the side that will contact the tree, bush, or rose during the treatment. The same strip may have glue or adhesive at one or both ends to wrap around or stick to the subject being treated.

The compositions according to the invention can be sprayed or dusted on the leaves in the form of pellets, spray solution, granules, or dust.

The solid or semi-solid compositions of the invention can be coated using film-coating compounds used in the pharmaceutical industry such as polyethylene glycol, gelatin, sorbitol, gum, sugar or polyvinyl alcohol. This is particularly essential for tablets or capsules used in pesticide formulations. Film coating can protect the handler from coming in direct contact with the active ingredient in the formulations.

In addition, a bittering agent such as denatonium benzoate or quassin may also be incorporated in the pesticidal formulations, the coating or both.

The compositions of the invention can also be prepared in powder formulations and filled into pre-manufactured gelatin capsules.

The concentrations of the ingredients in the formulations and application rate of the compositions may be varied widely depending on the pest, plant or area treated, or method of application. As described in greater detail below, the compositions and methods of the invention can be used to control a variety of pests, including insects and other invertebrates, algae, microbial pests, and, in some situations, weeds or other plants.

A purified mixture of rhamnolipids (supplied by Jeneil Biotech of Saukville, Wis.) and *Pseudomonas* spp. fermentation broth filtrate was tested for their activity on different pests such as thrips, aphids, houseflies, mosquitoes, box-elder bugs, nematodes, spider mites and algae. The cultured material was effective at a concentration as low as 0.005% on some pests. The following are examples to illustrate the procedures of practicing the invention. These examples are illustrative and should not be construed as limiting.

EXAMPLES

Fermentation broth containing rhamnolipids was tested for its effectiveness as insecticide to control houseflies. Ten houseflies were confined in petri dishes covered with screen through which the insecticide was sprayed. Another set of ten houseflies were sprayed with water and kept as control. Table 1 shows the results of the test.

TABLE 1

Effect of rhamnolipid treatments on housefly survival.

| | Rhamnolipid Treatments | |
| --- | --- | --- |
| | 0% | 3% |
| Time(min.) | Houseflies Survival Rate | |
| 2 | 100 | 100 |
| 5 | 100 | 90 |
| 7.5 | 100 | 70 |
| 10 | 100 | 30 |
| 12 | 100 | 20 |
| 15 | 100 | 0 |

In another test, purified rhamnolipid material at 2.5% concentration was sprayed directly on spiders in naturally infested area. Treatment included six spiders sprayed with the pesticide as a test, while six spiders were sprayed with water as control. Full control of the spider mites was achieved in less than fifteen minutes after treatment.

A naturally infested lemon tree with spider mites was sprayed with a 1.25% rhamnolipid solution. The mites were observed using magnifying glass for movement. Death was noted in less than 15 minutes.

Naturally infested tomato plants with whiteflies were sprayed with 0.1% rhamnolipid mixture diluted in water. Control plants were sprayed with water only. Whiteflies sprayed with the rhamnolipids stuck to the leaves and weren't able to move after the treatment. Full control was achieved in less than 6 minutes.

Into each 1-liter water bottle a tablet containing 0, 0.075, or 0.2 grams rhamnolipid (put example) was added. Ten-mosquitoes larvae were transferred into each of the bottles. Total death of the larva was observed in about 2 hours and 40 minutes in the bottle containing 0.2 grams rhamnolipid. In the bottle containing 0.075 grams rhamnolipid, only one live mosquito larva was left after 24 hours of study initiation. No death was observed in the control treatment. This significant discovery is critical in the control and spread of the West Nile Virus Vector. In another study we found that rhamnolipid addition at concentration of 100 ppm prevented mosquitoes eggs from hatching.

A Petri dish containing fifty ml of water infested with amoeba was treated with 250 ppm rhamnolipid. Examining the amoeba under the microscope before and after the treatment showed that within five minutes of rhamnolipid addition that the amoeba collapsed and disintegrated.

An infested red ants mound was drenched with 0.5% rhamnolipid solution. The treatment was effective and the mound was free of ants for more than 2 weeks.

Pesticidal Preparations:

Example A

A 5% rhamnolipid solution was prepared using 25% purified rhamnolipid concentrate supplied by Jeneil Biotech.

Example B

A concentrated solution was prepared by mixing 20 grams sesame oil, 30 grams canola oil, 10 grams glycerol, and 40 grams water. The mixture is diluted 10, 50 or 100 times with water prior to use.

Example C

A concentrated solution was prepared by mixing 5 grams rhamnolipids, 20 grams sesame oil, 30 grams canola oil, 10 grams glycerol, and 35 grams water. The mixture was diluted 10, 50, or 100 times with water prior to use.

Example D

Water used as a control treatment.

Example E

A concentrated Solution of 10% phosphite and 8% potassium was prepared by mixing 70% phosphorous acid, 45% potassium hydroxide, and water. The solution was buffered with citrate/gluconic acid to pH of 5.8. The mixture was diluted 100 times with water prior to use.

Example F

A concentrated Solution of 5% rhamnolipid, 10% phosphite and 8% potassium was prepared by mixing 70% phosphorous acid, 45% potassium hydroxide, and water. The solution was buffered with citrate/gluconic acid to pH of 5.8. The mixture was diluted 100 times with water prior to use.

Grasshopper Study:

For each treatment, six grasshoppers were sprayed with solutions prepared from Examples A, B, C, or D diluted 10 or 100 times with water. At ten times dilution, Example C treatment was the most effective and killed all the treated grasshoppers within ten minutes. Example A treatment at 10 times dilution instantly slowed down the movement of the grasshoppers, but half of the treated recovered within 20 minutes of application. Example B treatment at 10 times dilution had similar effect like that of rhamnolipid alone. At 100 times dilution, example A was not effective. Example B treatment was 33% effective and example C treatment was 84% effective. Water treatments had no effect on grasshoppers.

Powdery Mildew Study:

Diluted solutions of Examples A, B, C, or D were sprayed on squash and roses plants heavily infected with Powdery mildew. Results of rose treatments are presented in Table 2. It was interesting to note that upon spraying the roses with example C formulation at 100 times dilution, the infected area washed out completely from the leaves. The results of squash treatments were similar to rose treatments, but squash plants were more sensitive to the spray solutions. At 10 times dilution, squash leaves developed necrotic tissues within 24 hours of the spray application and the plants shut down and died within three days. Examples E and F were tested on roses only. An important finding in powdery mildew treatments is that neither rhamnolipid nor phosphite alone was very effective against the powdery mildew at the concentrations used; however, the rhamnolipid/phosphite combination was very effective in the treatment of powdery mildew disease. Although powdery mildew does not belong to the zoosporic fungi group, it is believed that the rhamnolipid enhances the activity and mode of action of phosphite through membrane disturbance or by penetrating the fungus protective layers.

TABLE 2

Effect of different formulations on the control of powdery mildew on roses.

| TREATMENT | DILUTION FACTOR | DISEASE SEVERITY* | CONTROL | PHYTO-TOXICITY** |
|---|---|---|---|---|
| EXAMPLE A | 10x | 4 | Limited suppression | 2 |
|  | 50x | 5 | No Effect | 1 |
|  | 100x | 5 | No Effect | 1 |
| EXAMPLE B | 10x | 2 | Effective suppression | 4 Total leaf burn |
|  | 50x | 4 | Limited Suppression | 3 |
|  | 100x | 4 | Limited Suppression | 2 Localized spots |
| EXAMPLE C | 10x | 2 | Effective suppression | 4 |
|  | 50x | 1 | Effective suppression | 2 |
|  | 100x | 1 | Very effective control | 1 |
| EXAMPLE D CONTROL | Water | 1 | No Effect | 1 |
| EXAMPLE E | 100x | 5 | No Effect | 1 |
| EXAMPLE F | 100x | 2 | Suppression for more than 10 days | 1 |

*Treated plants were visually examined for disease symptoms on the leaves. Evaluation was documented on scale of 1-5, where 1 = No Powdery Mildew, 2 = 1-25% infection, 3 = 26-50% infection, 4 = 51-75% infection, 5 = 76-100% infection (all the leaves are infected). Phyto-toxicity was documented on scale of 1-4 where 1 = No necrosis, 2 = 25% of leaf is necrotic, 3 = 50% leaf damage, and 4 = total leaf damage.

Herbicidal Activity:

Due to the powerful micro-emulsifying and penetrating activity of the biosurfactants, especially in combination with oil, they can be used as nonselective herbicides to control weed pests. At concentrations of 0.5% rhamnolipid and higher, necrosis was observed on some plants. This effect is extremely magnified in the presence of oil especially sesame or cottonseed oil. At a concentration of 0.05% rhamnolipid and 2% oil, many treated weeds or plants were destroyed within few days of the treatment.

Nematodes Treatment:

Preliminary tests on nematodes were conducted according to the following procedure. The soil used in this test was isolated from a potato field naturally infested with nematodes. Seventy-five grams of soil (15% initial water content) were wrapped in double folded piece of cheesecloth and fitted in a strainer. The strainer containing the soil was gently suspended in a plastic funnel containing 450 ml water (control), or 0.75% Rhamnolipid mixture. The bottom surface of the strainer containing the soil was maintained in contact with the treatment solutions throughout the study. Twenty-five ml samples were collected at different times through the clamped tubing connected to the stem of the funnel. The supernatant solutions were directly transferred to a petri dish for examination using a microscope. The number of nematode pests surviving was recorded at 24 hrs intervals for a period of seven days. Mortality was concluded if individual nematodes are immobile and fail to respond to disturbance with an eyelash cemented to a needle. The test was done in three replicates. The results are presented in Table 3.

TABLE 3

Effect of rhamnolipid mixture treatments on nematodes control.

| | Rhamnolipid Treatment | |
|---|---|---|
| Time (hrs) | 0% | 0.75% |
| | Total Nematode Control Rate (%) | |
| 24 | 7.7 | 16.3 |
| 48 | 23.1 | 35.4 |
| 72 | 27.7 | 48.3 |
| 96 | 34.6 | 60.5 |
| 120 | 39.2 | 74.8 |
| 144 | 47.7 | 93.0 |

Different formulations and concentrations have been tested for activity against potato, tomato, and sugar beet nematodes and other pests.

After the nematode experiment was terminated, a surprise finding was observed on the nematodes treatment solutions present in the plastic funnel. It was observed that the control (water only) solution supported the growth of algae after it was left in the sun for few weeks. On the contrary, rhamnolipid treatment maintained clear solution with no algae growth. To verify the results, another set of treatments at 0 (water as control), 0.005, 0.01, 0.1 and 1% rhamnolipid concentrations were conducted. The water used in the experiment was collected from an algae infested pond. All rhamnolipid treatments did not support the growth of algae. However, at the lowest concentration of rhamnolipid, algae growth was re-established after 6 weeks of the initiation of the study. The other treatments were clean of algae during the three months study. Control treatment (pond water) turned greenish in color and the algae flourished in the water.

Root Knot Eggs Nematode Study:

A set of nematode eggs taken from the roots of tomato plant infested with nematode galls were transferred into petri dishes containing either 25 ml water or 250 ppm rhamnolipid in 25 ml water. The eggs were periodically examined under the microscope. Rhamnolipid treated eggs' color changed to brownish color during the course of the study and the eggs collapsed and disintegrated after 7 days. No change in eggs' color or shape was observed in the water treatment.

Gel preparation: A 5% rhamnolipid Gel formulation is prepared by impregnating 1.0% gum or carboxyvinyl carbopol polymer with purified rhamnolipid dissolved in water. The material is mixed using a vortex to yield a paste in less than 30 minutes. This treatment can be used to rub on animals for Ticks treatment.

Figure 1:
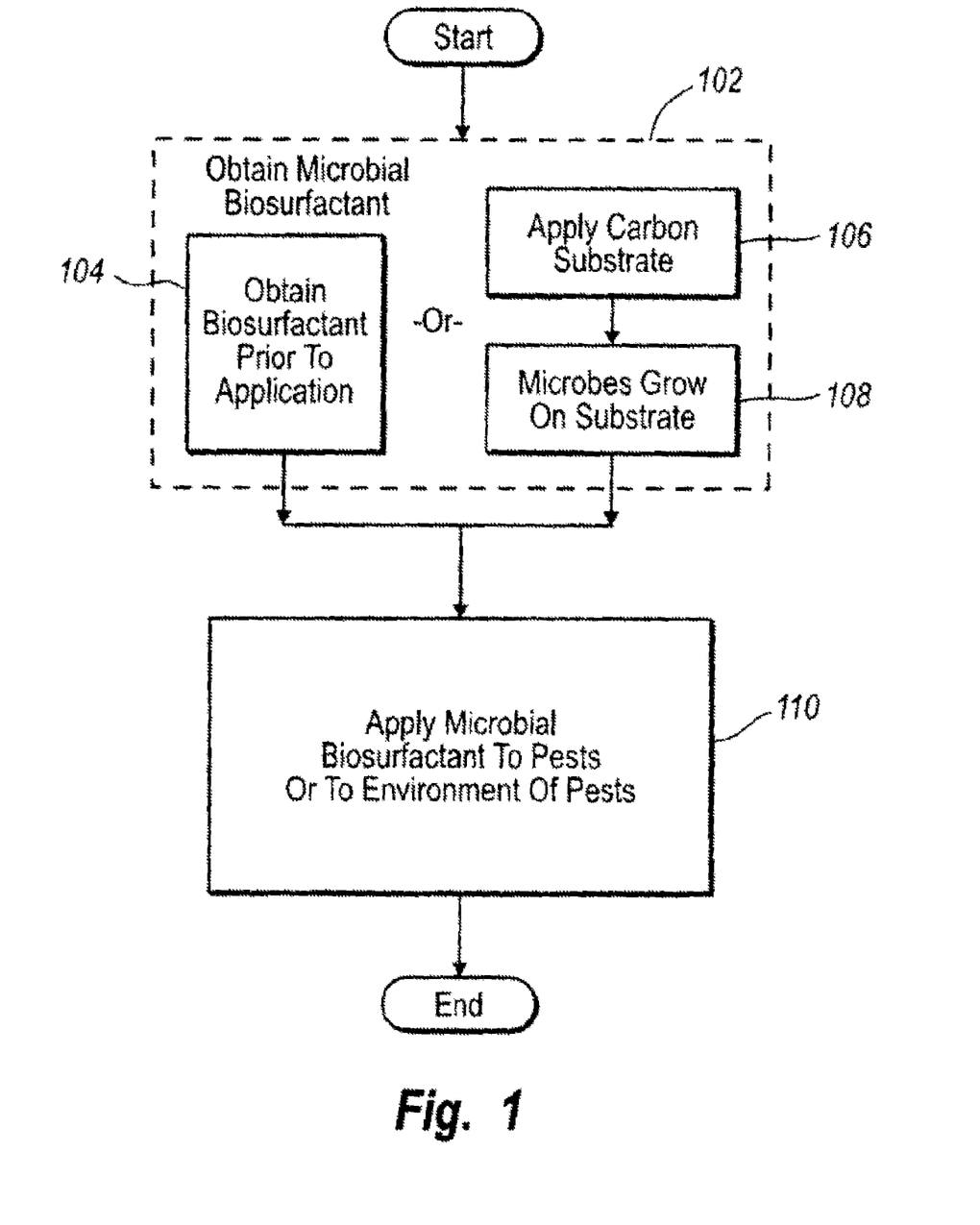
FIG. 1 is a flow diagram illustrating a method of applying microbial biosurfactants to control pests according to an embodiment of the invention.

FIG. 1 is a flow diagram that illustrates an example of the methods of the invention for controlling pests. The method begins by obtaining a microbial biosurfactant (102). As described herein, the biosurfactant can be obtained by a manufacturing or cultivation process that occurs prior to applying the biosurfactant (104). Alternately, the biosurfactant can be obtained by applying a carbon substrate to the environment of the pests (106) and permitting naturally-occurring microbes to grow on the substrate (108) and to thereby produce the biosurfactant. In either case, the biosurfactant is applied to the pests or to the environment of the pests (110), such that the pests are substantially controlled.

Figure 2:
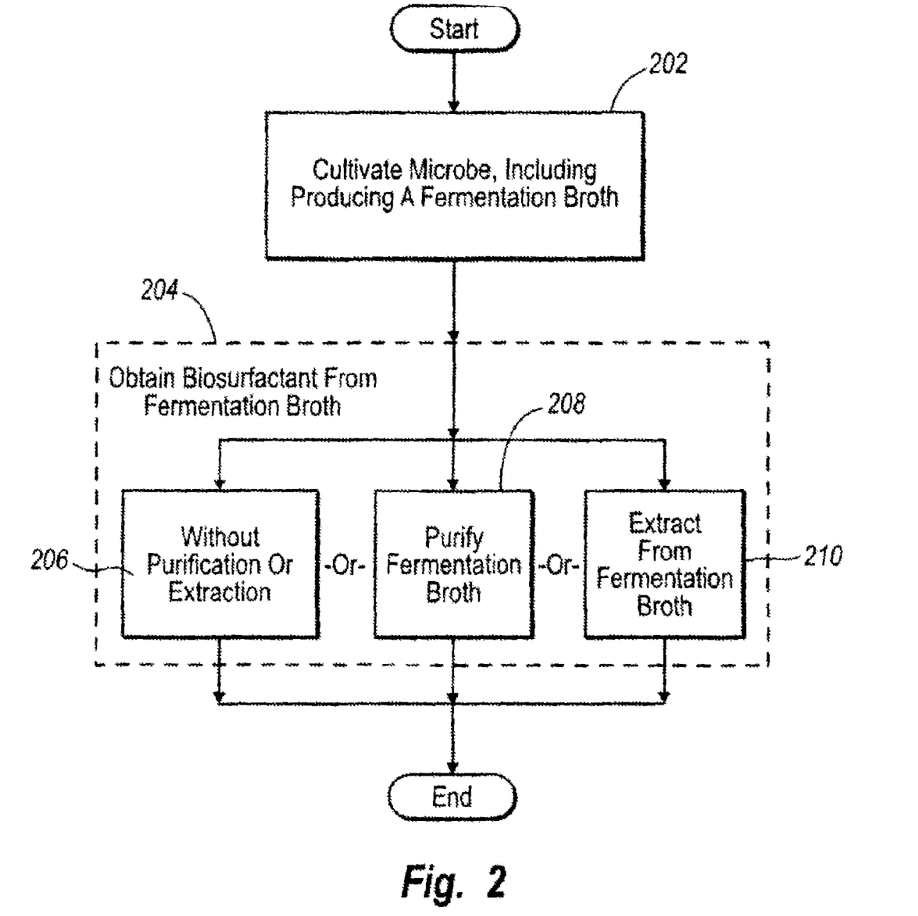
FIG. 2 is a flow diagram illustrating a method of obtaining biosurfactants in a concentration that is sufficient to be used to control pests.

FIG. 2 is a flow diagram that illustrates an example of the methods of the invention for producing biosurfactants that can be used to control pests. The method begins by cultivating a biosurfactant-producing microbe, including producing a fermentation broth containing the biosurfactant (202). The biosurfactant is then obtained (204) from the fermentation broth in a concentration that can be applied to pests or to an environment in which the pests are located in an amount such that the pests are substantially controlled. Obtaining the biosurfactant from the fermentation broth can be performed in one of a variety of ways illustrated in FIG. 2. For instance, in certain embodiments, the fermentation broth includes the biosurfactants at a suitable concentration (206) without requiring purification or extraction. Alternately, the fermentation broth can be purified (208) or the biosurfactant can be extracted from the fermentation broth (210). Although these exemplary methods illustrated in FIG. 2 are suitable for obtaining biosurfactants, the methods of controlling pests disclosed herein can be performed regardless of the methods used to obtain the biosurfactants.

The invention may be embodied in other specific forms without departing from its spirit or essential characteristics. The described embodiments are to be considered in all respects only as illustrative and not restrictive.

The processes, methods of use and examples of components listed in the invention are illustrative and not inclusive. The invention may be embodied in other specific forms without departing from its spirit or essential characteristics. The described embodiments are to be considered in all respects only as illustrative and not restrictive. The appended claims are presented to illustrate the embodiments of the invention disclosed herein.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an", should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims. All references recited herein are incorporated herein by specific reference in their entirety.

The invention claimed is:

1. A method for controlling pests, comprising:
   obtaining a microbial biosurfactant having a glycolipid; and
   providing the microbial biosurfactant to one or more pests in an amount such that the one or more pests are substantially controlled, wherein the pests are selected from box-elder bugs, ants, grasshoppers, weed plants, eggs thereof, larva thereof, or combinations thereof.

2. The method as defined in claim 1, wherein obtaining a biosurfactant comprises cultivating a microbe that produces the biosurfactant, the cultivating including producing a fermentation broth containing the biosurfactant.

3. The method as defined in claim 2, wherein cultivating the microbe further comprises purifying the fermentation broth or extracting the biosurfactant from the fermentation broth.

4. The method as defined in claim 1, wherein the microbial biosurfactant has been produced by a microbe selected from:
   *P. aeruginosa, P. putida, P. florescens, P. fragi*, and *P. syringae;*
   *flavobacterium* species;
   *C. albicans, C. rugosa, C. tropicalis, C. lipolytica*, and *C. torulopsis;*
   *rhodococcus* species;
   *arthrobacter* species;
   *campylobacter* species; or
   *cornybacterium* species.

5. The method as defined in claim 1, wherein the microbial biosurfactant is a penetrant that penetrates the pest without the use of a separate adjuvant.

6. The method as defined in claim 1, wherein the microbial biosurfactant is combined with a solubility control agent.

7. The method as defined in claim 6, wherein the solubility control agent is a cross-linked swellable polyacrylamide.

8. The method as defined in claim 1, wherein the biosurfactant is combined with an oil.

9. The method as defined in claim 1, wherein the biosurfactant is in a formulation having a form selected from the group consisting of liquid, solutions, suspensions, powders, pastes, waxes, gel, cream, cylinders, rods, blocks, capsules, tablets, pills, pellets, strips, or spikes.

10. The method as defined in claim 9, wherein the formulation is provided to an environment in which the pest is located, the environment is selected from an ant mound, soil, plant, aquatic medium, a structure, or combinations thereof.

11. The method as defined in claim 1, wherein the controlled pests are killed or paralyzed.

12. The method as defined in claim 1, wherein the microbial biosurfactant includes a rhamnolipid and/or a sophorlipid.

13. The method as defined in claim 1, wherein the biosurfactant is included in a composition that also includes lipopeptides, flavolipids, phospholipids, lipoproteins, lipopolysaccharide-protein complexes, oils, fats, lipids, waxes, fatty acids, fatty acid alcohols, amphiphilic esters of fatty acids with glycerol, glycol esters of fatty acids, fatty acid amines, hexanes, glycerols, glucose, alkyl betaines, alkyl sulfates, alkyl ammonium bromide derivatives, alkyl phenol ethoxylates, alkyl ethylene ethoxylates, polyethylene ethoxylates, or combinations thereof.

14. A method for controlling pests, comprising:
obtaining a microbial biosurfactant having a glycolipid; and
providing the microbial biosurfactant to one or more pests in an amount such that the one or more pests are substantially controlled, wherein the pests are arachnids or eggs thereof or larva thereof.

15. A method for controlling pests, comprising:
obtaining a composition having an oil and a microbial biosurfactant having a glycolipid; and
providing the composition to one or more pests in an amount such that the one or more pests are substantially controlled, wherein the pests are weed plants.

16. The method as defined in claim 1, wherein the pest is ants, eggs thereof, larva thereof, or combinations thereof.

17. The method as defined in claim 1, wherein the pest is grasshoppers, eggs thereof, larva thereof, or combinations thereof.

18. The method as defined in claim 1, wherein the pest is box-elder bugs, eggs thereof, larva thereof, or combinations thereof.

* * * * *